US00PP16440P2

(12) United States Plant Patent

Iwaki et al.

(10) Patent No.: US PP16,440 P2
(45) Date of Patent: Apr. 11, 2006

(54) *PETUNIA* PLANT NAMED 'SUNRASPBERRY'

(50) Latin Name: *Petunia×hybrida*
Varietal Denomination: Sunraspberry

(75) Inventors: Kazunari Iwaki, Shiga (JP); Takuro Ishihara, Tokyo (JP); Shinya Miyano, Tounosyou-machi (JP)

(73) Assignee: Suntory Flowers Limited, Tokyo (JP)

( * ) Notice: Subject to any disclaimer, the term of this patent is extended or adjusted under 35 U.S.C. 154(b) by 49 days.

(21) Appl. No.: 11/050,886

(22) Filed: Feb. 5, 2005

(51) Int. Cl.
*A01H 5/00* (2006.01)

(52) U.S. Cl. ..... Plt./356
(58) Field of Classification Search ..... Plt./356
See application file for complete search history.

(56) References Cited

U.S. PATENT DOCUMENTS

PP9,341 P * 10/1995 Tachibana et al. ..... Plt./356
PP13,778 P2 * 5/2003 Westhoff ..... Plt./356
PP14,125 P2 * 9/2003 Miyazaki ..... Plt./356

OTHER PUBLICATIONS

UPOV ROM Computer Database, GTI Jouve Retrieval Software 2005/02 Citations for 'Sunraspberry'.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Petunia* plant named 'Sunraspberry', characterized by its outwardly spreading and decumbent plant habit; vigorous and freely branching growth habit; relatively small leaves; numerous light pink-colored flowers with red purple-colored venation; long flowering period; and good garden performance.

1 Drawing Sheet

Botanical designation: *Petunia×hybrida.*
Cultivar denomination: 'Sunraspberry'.

CROSS REFERENCE TO RELATED APPLICATIONS

The present application is co-pending with U.S. Plant patent application Ser. No. 11/050,885, *Petunia* Plant Named 'Sunmilk'.

BACKGROUND OF THE INVENTION

The present Invention relates to a new and distinct cultivar of *Petunia* plant, botanically known as *Petunia×hybrida,* and hereinafter referred to by the cultivar name Sunraspberry.

The new *Petunia* is a product of a planned breeding program conducted by the Inventors in Yokaichi, Shiga, Japan. The objective of the breeding program is to create new *Petunias* with numerous flowers with attractive flower colors.

The new *Petunia* originated from a cross-pollination made by the Inventors in December, 2000 of a proprietary *Petunia* selection identified as code number PF 165-1, not patented, as the female, or seed parent, with a proprietary *Petunia* selection identified as code number PF 171-1, not patented, as the male, or pollen parent. The new *Petunia* was selected as a single plant from the resulting progeny of the cross-pollination by the Inventors in a controlled environment in Yokaichi, Shiga, Japan.

Asexual reproduction of the new cultivar by terminal cuttings in a controlled environment in Yokaichi, Shiga, Japan since October, 2003 has shown that the unique features of this new *Petunia* are stable and reproduced true to type in successive generations.

SUMMARY OF THE INVENTION

Plants of the cultivar Sunraspberry have not been observed under all possible environmental conditions. The phenotype may vary somewhat with variations in environment such as temperature and light intensity without, however, any variance in genotype.

The following traits have been repeatedly observed and are determined to be the unique characteristics of 'Sunraspberry'. These characteristics in combination distinguish 'Sunraspberry' as a new and distinct *Petunia* cultivar:

1. Outwardly spreading and decumbent plant habit.
2. Vigorous and freely branching growth habit.
3. Relatively small leaves.
4. Numerous light pink-colored flowers with red purple-colored venation.
5. Long flowering period.
6. Good garden performance.

Plants of the new *Petunia* differ from plants of the female and male parent selections in the following characteristics:

1. Plants of the new *Petunia* are broader than plants of the female or the male parent selection.
2. Plants of the new *Petunia* have obtuse-shaped petals whereas plants of the female and male parent selections have truncate-shaped petals.
3. Plants of the new *Petunia* and the female and male parent selections differ in flower coloration.

Plants of the new *Petunia* can be compared to plants of the cultivar Sunrove, disclosed in U.S. Plant Pat No. 14,125. In side-by-side comparisons conducted in Yokaichi, Shiga, Japan, plants of the new *Petunia* differed from plants of the cultivar Sunrove in the following characteristics:

1. Plants of the new *Petunia* were not as broad as plants of the cultivar Sunrove.
2. Plants of the new *Petunia* had smaller leaves than plants of the cultivar Sunrove.
3. Plants of the new *Petunia* had smaller flowers than plants of the cultivar Sunrove.
4. Plants of the new *Petunia* and the cultivar Sunrove differed in flower coloration.
5. Plants of the new *Petunia* flowered longer than plants of the cultivar Sunrove.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a side perspective view of a typical flowering plant of 'Sunraspberry' grown in a container.

The photograph at the bottom of the sheet comprises a close-up view of typical flowers of 'Sunraspberry'.

DETAILED BOTANICAL DESCRIPTION

The aforementioned photographs and following observations and measurements describe plants grown in Yokaichi, Shiga, Japan, in an outdoor nursery during the summer with day temperatures about 22° C. and night temperatures about 12° C. Plants were grown for four months in 15-cm containers. Plants were pinched one time in the spring. Color references are made to The Royal Horticultural Society Colour Chart, 2001 Edition, except where general terms of ordinary dictionary significance are used.

Botanical classification: *Petunia×hybrida* cultivar Sunraspberry.

Parentage:

*Female parent.*—Proprietary *Petunia* selection identified as code number PF 165-1, not patented.

*Male parent.*—Proprietary *Petunia* selection identified as code number PF 171-1, not patented.

Propagation:

*Type cutting.*—Terminal vegetative cuttings.

*Time to initiate roots.*—About one week at 18° C.

*Time to develop roots.*—About three weeks at 18° C.

*Root description.*—Fine, fibrous, fleshy; light brown in color.

*Rooting habit.*—Freely branching.

Plant description:

*Form.*—Annual flowering plant; indeterminate; outwardly spreading and decumbent plant habit. Viscid and glandular pubescent. Vigorous growth habit.

*Branching habit.*—Freely branching habit with lateral branches developing potentially at every node.

*Plant height.*—About 10.6 cm.

*Plant diameter.*—About 26.9 cm.

*Lateral branches.*—Length: About 14 cm. Diameter: About 1.7 mm. Internode length: About 1.4 cm. Texture: Pubescent. Color: 146A.

*Foliage description.*—Arrangement: Alternate, simple; sessile. Length: About 2.9 cm. Width: About 1.9 cm. Shape: Elliptic. Apex: Acute. Base: Cuneate. Margin: Entire. Texture, upper and lower surfaces: Sparsely pubescent; viscid. Venation pattern: Pinnate; reticulate. Color: Developing and fully expanded foliage, upper surface: 146A. Developing and fully expanded foliage, lower surface: 144A. Venation, upper and lower surfaces: Similar to lamina.

Flower description:

*Flower type and habit.*—Single salverform flowers; flowers face mostly upward or outward; axillary. Flowers not persistent. Freely flowering habit.

*Natural flowering season.*—Plants flower from spring through late autumn in Japan; flowering continuous during this period.

*Flower longevity on the plant.*—About five days.

*Fragrance.*—None detected.

*Flower size.*—Diameter: About 4.5 cm. Length: About 5 cm.

*Flower buds.*—Length: About 4 cm. Diameter: About 1 cm. Shape: Cylindrical. Color: N155B.

*Corolla.*—Quantity/arrangement: Five petals; fused, funnelform. Petal shape: Roughly spatulate or fan-shaped. Petal apex: Cuspidate. Petal margin: Entire. Petal texture, upper and lower surfaces: Smooth; satiny. Color: Petal, upper surface, when developing and fully expanded: 62D; venation, 78B. Petal, lower surface, when developing and fully expanded: N155B; venation, 79B. Flower throat (inside): 154C. Flower tube (outside): 144D.

*Sepals.*—Arrangement/appearance: Single whorl of five sepals fused at base, star-shaped. Length: About 1 cm. Width: About 3 mm. Shape: Oblong. Apex: Obtuse. Margin: Entire. Texture, upper and lower surfaces: Pubescent. Color, immature and mature, upper surface: 146A. Color, immature and mature, lower surface: 146B.

*Peduncles.*—Length: About 1.6 cm. Width: About 0.9 mm. Strength: Moderately strong. Texture: Pubescent. Color: 144A.

*Reproductive organs.*—Stamens: Quantity: Five per flower. Anther shape: Ellipsoidal. Anther length: About 2 mm. Anther color: 147D. Pollen amount: Moderate. Pollen color: 1C. Pistils: Quantity: One per flower. Pistil length: About 2 cm. Style length: About 1.8 cm. Style color: 145B. Stigma shape: Broadly elliptic. Stigma color: 146C. Ovary color: 144A.

*Seed/fruit.*—Seed and fruit development have not been observed.

Disease/pest resistance: Plants of the new *Petunia* have not been noted to be resistant to specific pathogens and pests common to *Petunia*.

Garden performance: Plants of the new *Petunia* have been observed to have good garden performance and tolerate rain, wind and tolerated temperatures from 5° C. to 35° C.

It is claimed:

1. A new and distinct cultivar of *Petunia* plant named 'Sunraspberry', as illustrated and described.

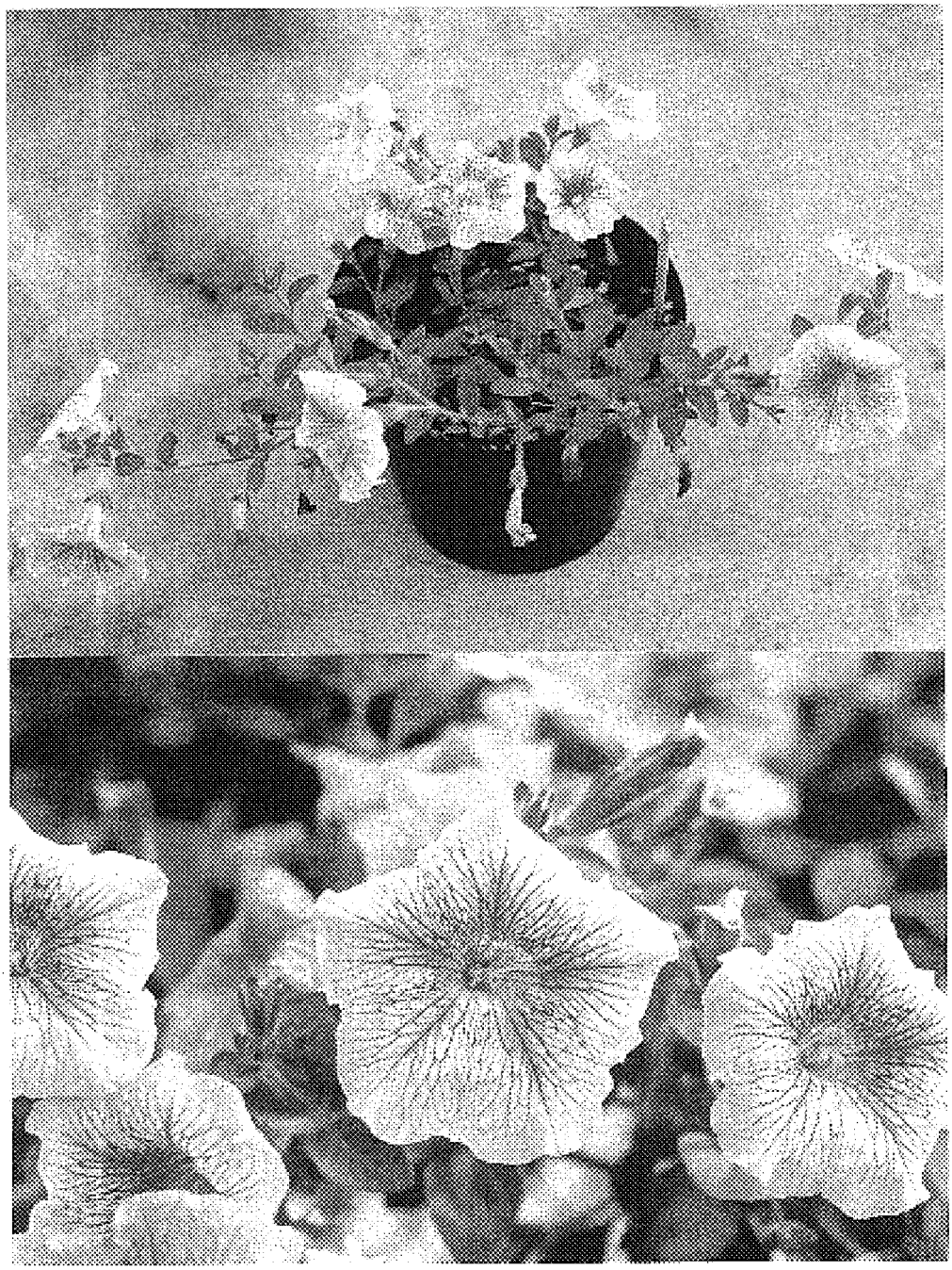

* * * * *